United States Patent
Limon

(10) Patent No.: US 7,163,553 B2
(45) Date of Patent: Jan. 16, 2007

(54) INTRAVASCULAR STENT AND METHOD OF USE

(75) Inventor: Timothy A. Limon, Cupertino, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 177 days.

(21) Appl. No.: 10/034,208

(22) Filed: Dec. 28, 2001

(65) Prior Publication Data

US 2003/0125799 A1 Jul. 3, 2003

(51) Int. Cl.
A61F 2/06 (2006.01)

(52) U.S. Cl. .................................... 623/1.15

(58) Field of Classification Search ........ 623/1.11–1.2, 623/1.35
See application file for complete search history.

(56) References Cited

U.S. PATENT DOCUMENTS

| | | | | |
|---|---|---|---|---|
| 5,755,781 | A * | 5/1998 | Jayaraman | 623/1.16 |
| 5,855,600 | A | 1/1999 | Alt | |
| 5,924,997 | A | 7/1999 | Campbell | |
| 6,129,754 | A * | 10/2000 | Kanesaka et al. | 623/1.15 |
| 6,245,026 | B1 | 6/2001 | Campbell et al. | |
| 6,273,910 | B1 | 8/2001 | Limon | |
| 6,325,826 | B1 * | 12/2001 | Vardi et al. | 623/1.35 |
| 6,450,971 | B1 | 9/2002 | Andrus et al. | |
| 6,451,044 | B1 | 9/2002 | Naghavi et al. | |
| 6,860,900 | B1 * | 3/2005 | Clerc et al. | 623/1.35 |
| 2001/0032011 | A1 | 10/2001 | Stanford | |
| 2001/0047138 | A1 | 11/2001 | Kokate et al. | |
| 2002/0009535 | A1 | 1/2002 | Michal et al. | |
| 2002/0062147 | A1 | 5/2002 | Yang | |
| 2002/0077564 | A1 | 6/2002 | Campbell et al. | |
| 2002/0082515 | A1 | 6/2002 | Campbell et al. | |
| 2002/0091436 | A1 | 7/2002 | Phelps et al. | |
| 2002/0107561 | A1 | 8/2002 | Pinheiro | |
| 2002/0128706 | A1 * | 9/2002 | Osypka | |
| 2002/0151959 | A1 * | 10/2002 | Von Oepen | |
| 2002/0183763 | A1 | 12/2002 | Callol et al. | |
| 2003/0125802 | A1 * | 7/2003 | Callol et al. | |

FOREIGN PATENT DOCUMENTS

WO WO 01/82835 A2 11/2001

OTHER PUBLICATIONS

Garasic, Joseph M., M.D., et al., *Stent and Artery Geometry Determine Intimal Thickening Independent of Arterial Injury*, Circulation, Feb. 22, 2000, pp. 812-818.
U.S. Appl. No. 10/222,731, filed Aug. 16, 2002 to Cox.
U.S. Appl. No. 10/280,632, filed Oct. 25, 2002 to Cox.

* cited by examiner

Primary Examiner—(Jackie) Tan-Uyen T. Ho
(74) Attorney, Agent, or Firm—Fulwider Patton LLP

(57) ABSTRACT

An expandable stent is implanted in a body lumen, such as a coronary artery, peripheral artery, or other body lumen for treating an area of vulnerable plaque. The invention provides for a an intravascular stent having a plurality of cylindrical rings connected by undulating links. The stent has a high degree of flexibility in the longitudinal direction, yet has adequate vessel wall coverage and radial strength sufficient to hold open an artery or other body lumen. A central section is positioned between distal and proximal sections and is aligned with the area of vulnerable plaque to enhance growth of endothelial cells over the fibrous cap of the vulnerable plaque to reinforce the area and reduce the likelihood of rupture.

63 Claims, 7 Drawing Sheets

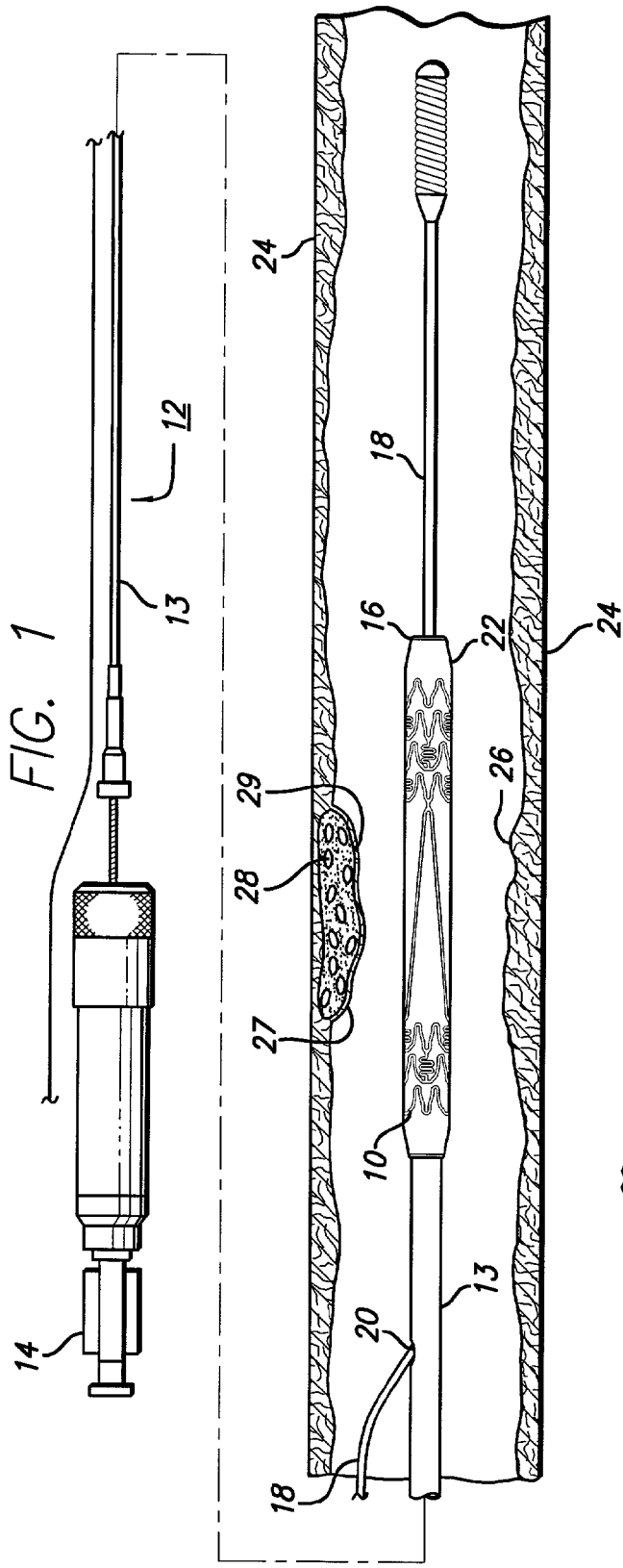
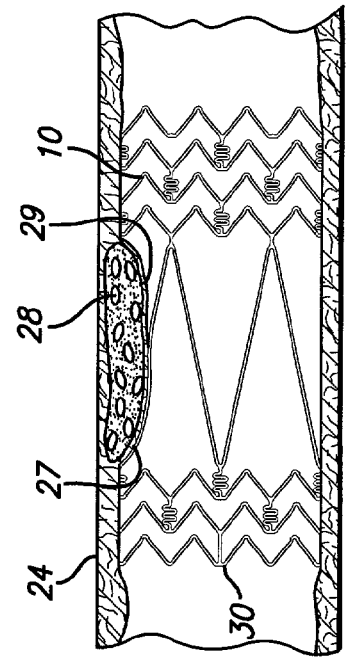
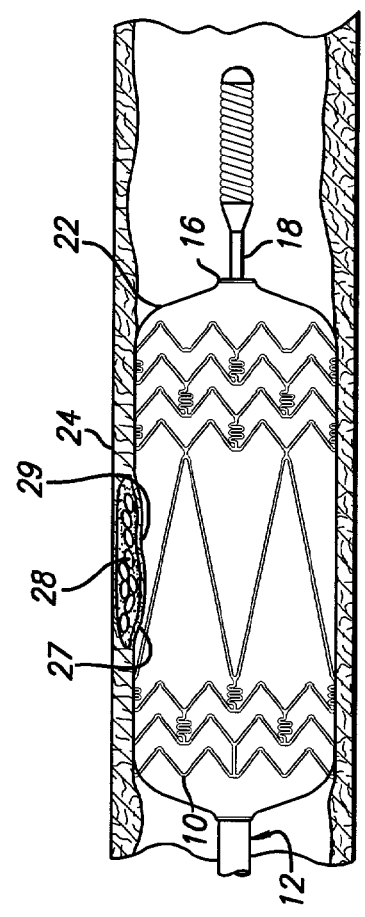

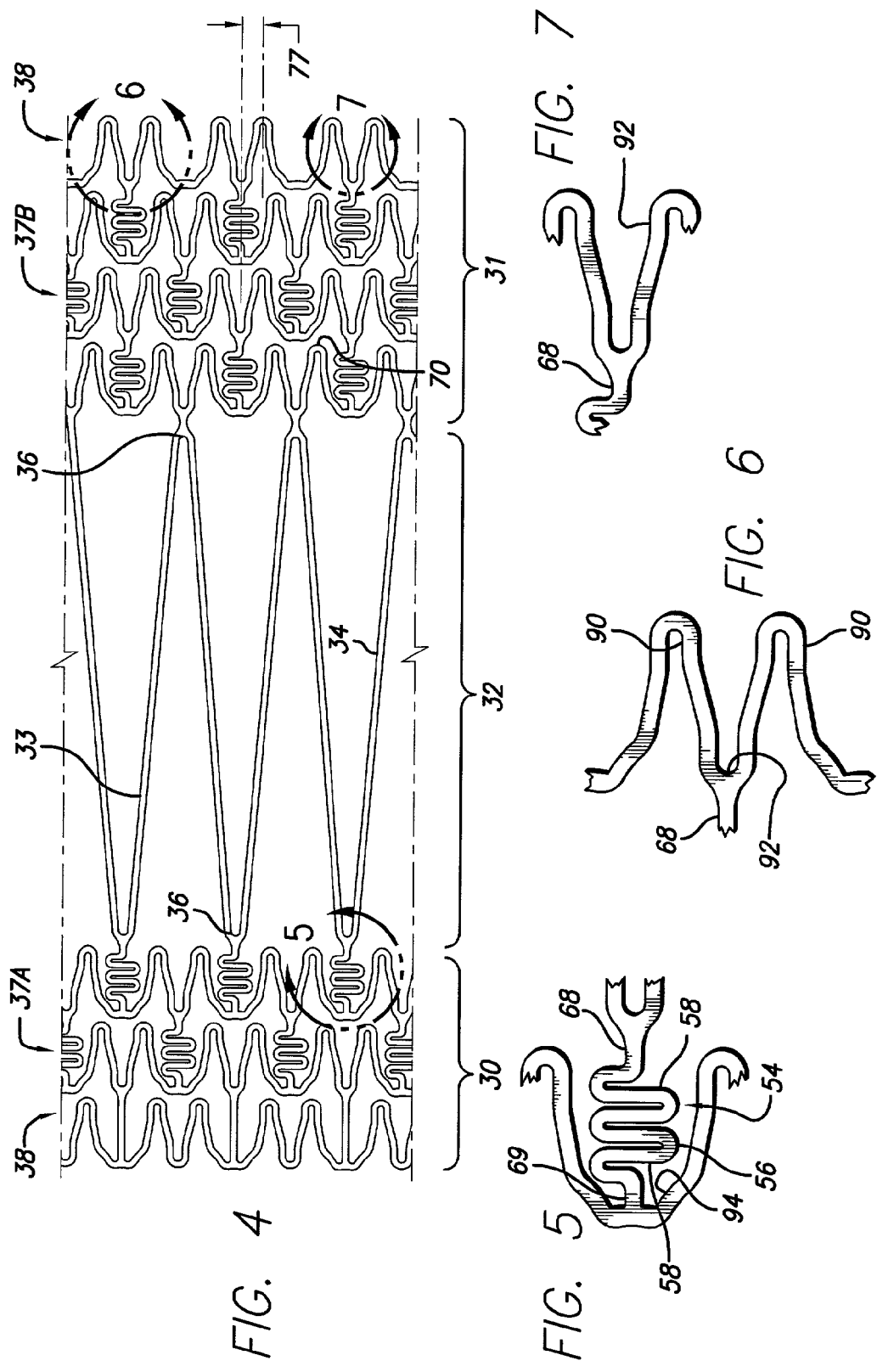

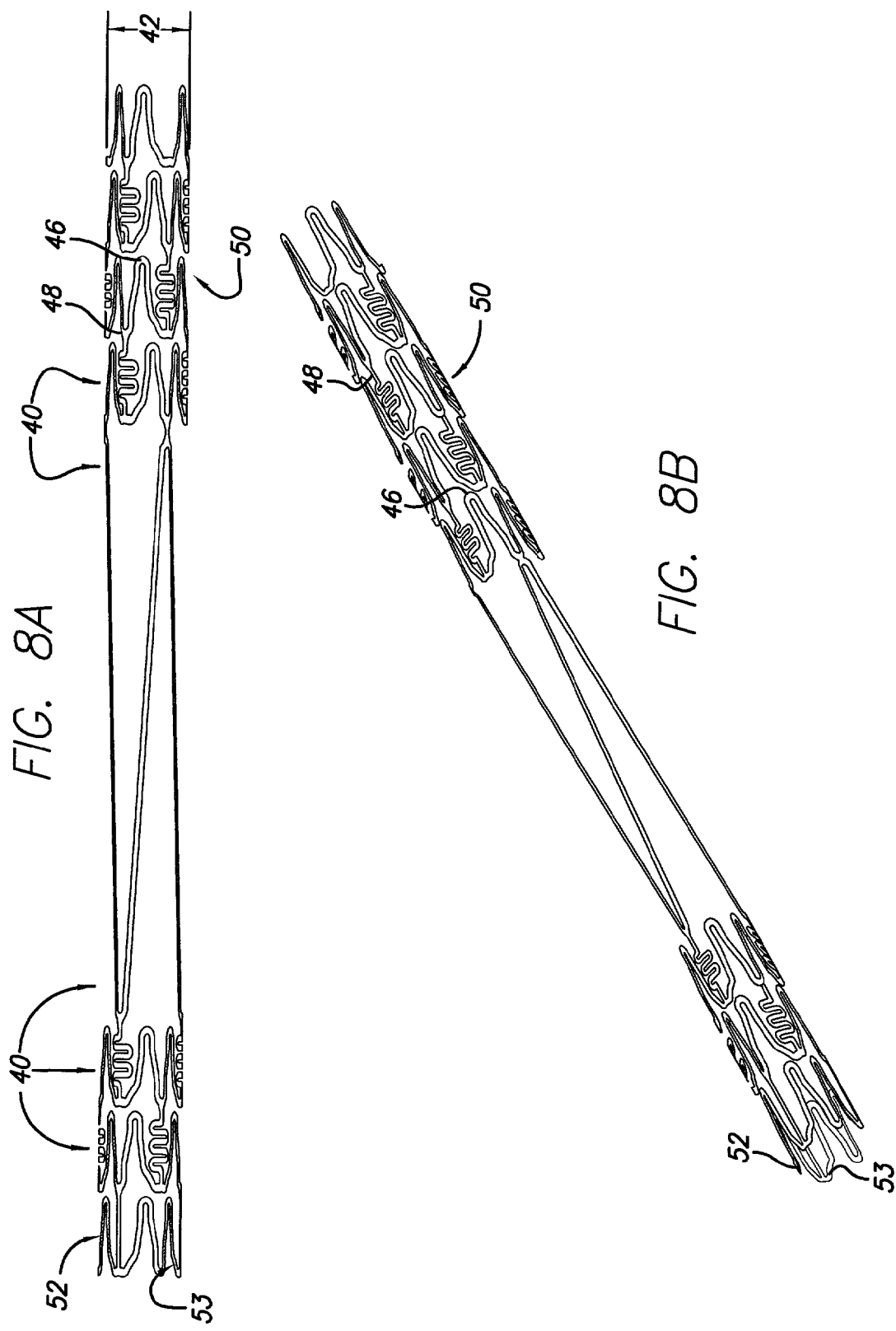

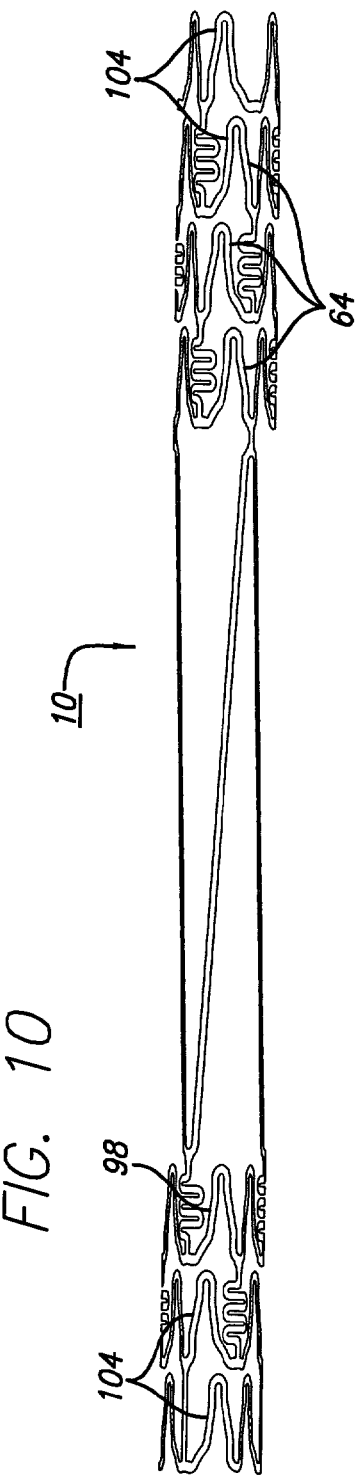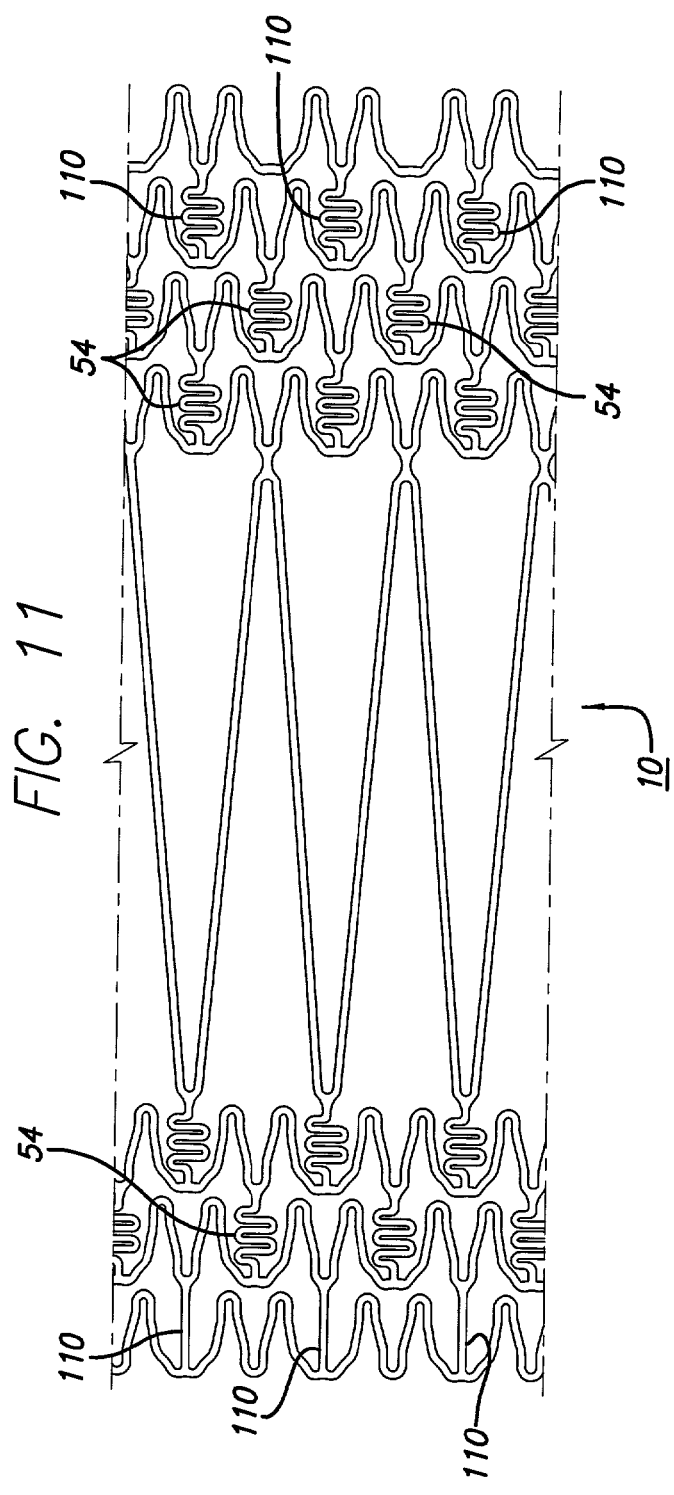
FIG. 10
FIG. 11

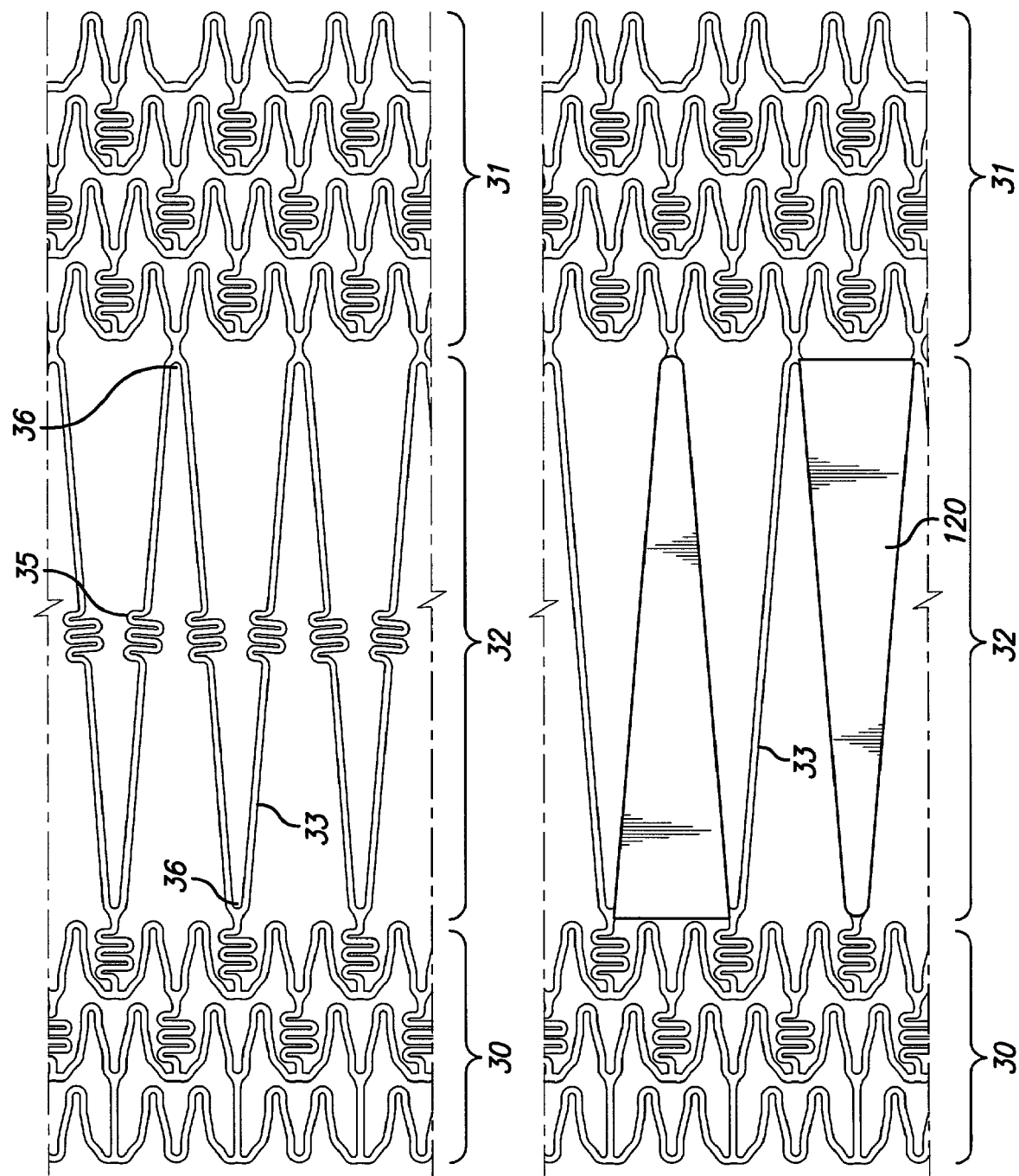

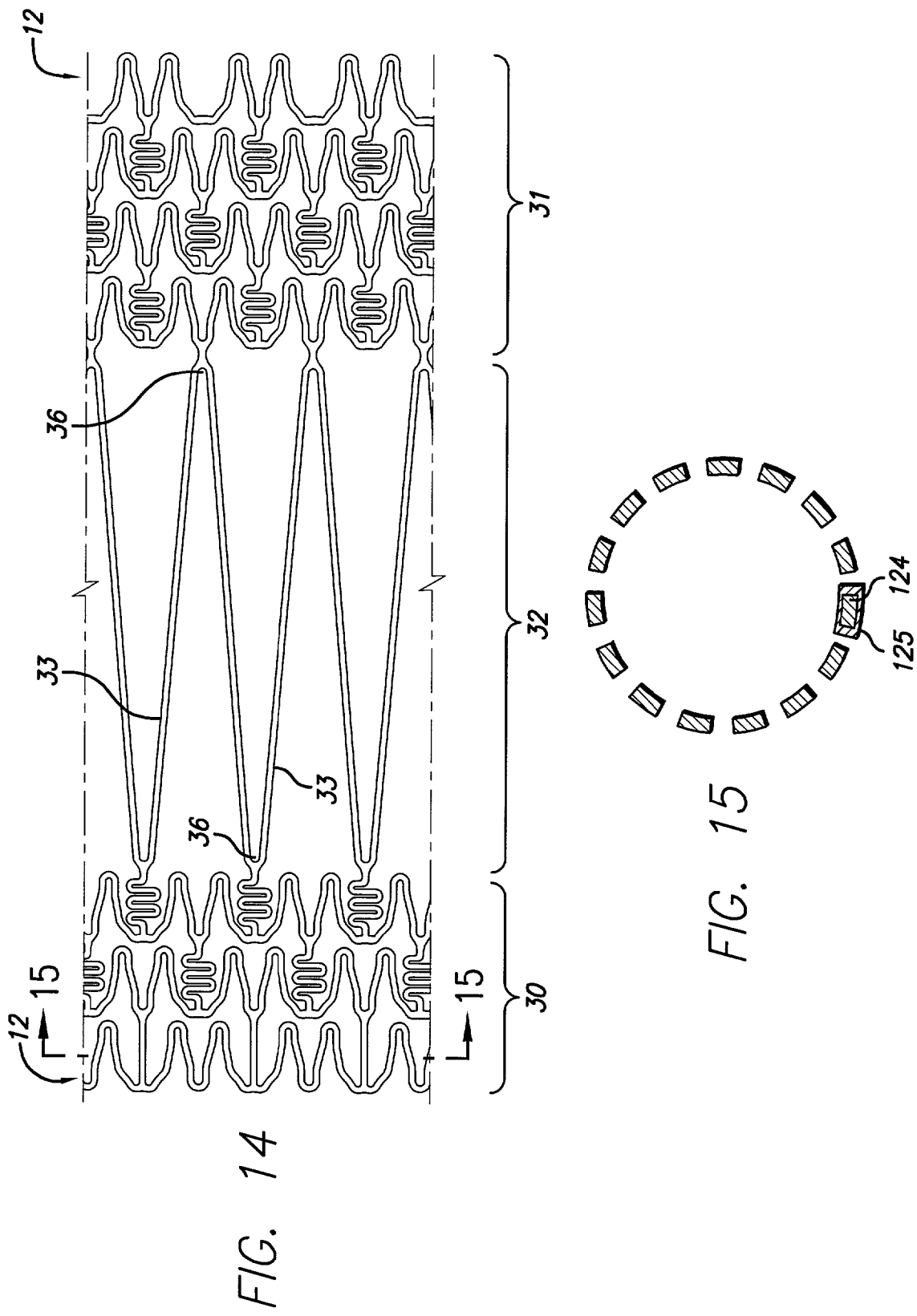

INTRAVASCULAR STENT AND METHOD OF USE

BACKGROUND OF THE INVENTION

This invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels.

Stents are generally tubular-shaped devices which function to hold open a segment of a blood vessel or other body lumen such as a coronary artery. They also are suitable for use to support and hold back a dissected arterial lining that can occlude the fluid passageway. At present, there are numerous commercial stents being marketed throughout the world. While some of these stents are flexible and have the appropriate radial rigidity needed to hold open a vessel or artery, there typically is a tradeoff between flexibility and radial strength.

Further, some coronary arteries may develop vulnerable plaque which may require treatment through stenting. What has been needed and heretofore unavailable is a stent which has a high degree of flexibility so that it can be advanced through tortuous passageways and can be readily expanded, and yet have the mechanical strength to hold open the body lumen or artery into which it is implanted and provide adequate vessel wall coverage at selected areas. What also has been needed is a stent that selectively reduces cell growth in one area, but enhances cell growth in other areas too, for example, cover the thin fibrous cap covering vulnerable plaque. The present invention satisfies these needs. The stent of the present invention has a high degree of flexibility making it possible to advance the stent easily through tortuous arteries, yet the stent has sufficient radial rigidity so that it can hold open an artery or other blood vessel, provide adequate vessel wall coverage, and enhance endothelial cell growth to reinforce the fibrous cover over any vulnerable plaque.

SUMMARY OF THE INVENTION

The present invention is directed to an intravascular stent which is highly flexible along its longitudinal axis to facilitate delivery through tortuous body lumens, but which is stiff and stable enough radially in its expanded condition to maintain the patency of a body lumen such as an artery when the stent is implanted therein. The novel stent pattern of the invention is particularly well suited for treating and repairing vulnerable plaque located in, for example, the coronary arteries.

The stent of the present invention generally includes a plurality of cylindrical rings that are interconnected to form a distal section and a proximal section, with a central section therebetween. The stent typically is mounted on a balloon catheter if it is balloon expandable or mounted on a catheter without a balloon if it is self expanding.

In one embodiment of the invention, the stent has a distal and proximal section formed of rings or cylindrical elements and links. The rings and links are configured so that the air to metal ratio is less than 90% and preferably less than about 80% thus providing good scaffolding and providing a more cylindrical lumen. A central section is formed of stent struts that join the distal and proximal sections together. The central section strut pattern is less dense than the rings and links pattern of the distal and proximal sections. This central section scaffolds less, making the lumen less cylindrical. In use, the central section is aligned with an area of vulnerable plaque so that as smooth muscle cell growth occurs after the stent is implanted, in an attempt to form a cylindrical lumen, the central section strut pattern promotes cell growth over the struts and hence over the fibrous cap of the vulnerable plaque. This cell layer acts to protect the vulnerable plaque from rupturing and possibly embolising in the artery. Comparatively, the rings and links pattern of the distal and proximal sections inhibit smooth muscle cell growth thereby maintaining a patent lumen for blood flow. Thus, the present invention stent promotes cell growth where needed, to cover and reinforce the vulnerable plaque area, and inhibits cell growth in other areas so that the lumen (artery) remains patent for maximum blood flow.

The central section of the stent includes struts that connect the distal and proximal section together. The central section struts can take different configurations and still function to hold open the vessel and promote cell growth. In one embodiment the struts are substantially straight and form a cylindrical zig-zag pattern. In another embodiment the central section struts have straight portions and curved portions which enhance stent flexibility. In yet another embodiment, the struts are curved or undulating. The length of the central section struts for all of the embodiments will depend on the length of the vulnerable plaque area to be repaired. If the plaque area is 6 to 8 mm in length, then the struts of the central section would be of a similar length or slightly longer. Typically, a coronary stent might be 18 mm long, therefore in one example, the central section struts would be 8 mm long and the distal and proximal sections each would be about 5 mm.

The cylindrical rings and links can have various configurations. In one embodiment, each of the cylindrical rings making up the stent have a proximal end and a distal end and a cylindrical plane defined by a cylindrical outer wall surface that extends circumferentially between the proximal end and the distal end of the cylindrical ring. The cylindrical rings are interconnected by at least one undulating link which attaches one cylindrical ring to an adjacent cylindrical ring. The undulating links are highly flexible and allow the stent to be highly flexible along its longitudinal axis. The undulating links are positioned substantially within the cylindrical plane of the outer wall surface of the cylindrical rings. The design of the highly flexible interconnecting members and their placement nested within a W-shaped member provides for uniform scaffolding and a high degree of vessel wall coverage at the proximal and distal sections.

The undulating links may take various configurations but in general have a undulating or serpentine shape. The undulating links can include bends connected by substantially straight portions wherein the substantially straight portions are substantially perpendicular to the stent longitudinal axis.

Not only do the undulating links that interconnect the cylindrical rings provide flexibility to the stent, but the positioning of the links also enhances the flexibility by allowing uniform flexibility when the stent is bent in any direction along its longitudinal axis. Further, the cylindrical rings are configured to provide flexibility to the stent in that portions of the rings can flex or bend and tip outwardly as the stent is delivered through a tortuous vessel.

In one embodiment of the invention, the cylindrical rings are connected by undulating links as described. In another embodiment, the rings are connected by substantially straight links, or continuation of straight links and undulating links. The number, amplitude and shape of the undulations in the links also can vary.

The cylindrical rings typically are formed of a plurality of peaks and valleys, where the valleys of one cylindrical ring are circumferentially offset from the valleys of an adjacent cylindrical ring. In this configuration, at least one undulating link attaches each cylindrical ring to an adjacent cylindrical ring so that the undulating links are positioned substantially within one of the valleys and it attaches the valley to an adjacent peak.

While the cylindrical rings and undulating links generally are not separate structures, they have been conveniently referred to as rings and links for ease of identification. Further, the cylindrical rings can be thought of as comprising a series of U's, W's and Y-shaped structures in a repeating pattern. Again, while the cylindrical rings are not divided up or segmented into U's, W's and Y's, the pattern of the cylindrical rings resemble such configuration. The U's, W's and Y's promote flexibility in the stent primarily by flexing and by tipping radially outwardly as the stent is delivered through a tortuous vessel.

The undulating links are positioned so that the undulating portion is within the curved part of the W-shaped portion which generally increases the amount of vessel wall coverage. Since the undulating portion does not substantially expand (if at all) when the stent is expanded, it will continue to provide good vessel wall coverage even as the curved part of the W-shaped portion spreads apart as the stent is expanded.

The cylindrical rings and the zig-zag shaped central section of the stent are plastically deformed when expanded when the stent is made from a metal that is balloon expandable. Typically, the balloon expandable stent is made from a stainless steel alloy or similar material.

Similarly, the cylindrical rings and the zig-zag struts of the central section of the stent expand radially outwardly when the stent is formed from a superelastic alloy, such as nickel titanium (NiTi). In the case of superelastic alloys, the stent expands upon application of a temperature change or when a stress is relieved, as in the case of a pseudoelastic phase change.

The number and location of undulating links that interconnect adjacent cylindrical rings can be varied as the application requires. Since the undulating links typically do not expand when the cylindrical rings of the stent expand radially outwardly, the links continue to provide flexibility and to also provide a scaffolding function to assist in holding open the artery. Importantly, the addition or removal of the undulating links has very little impact on the overall longitudinal flexibility of the stent. Each undulating link is configured so that it promotes flexibility whereas prior art links actually reduce flexibility of the stent.

Because of the undulating configuration of the links, the stent has a high degree of flexibility along the stent axis, which reduces the tendency of stent fishscaling. Stent fishscaling can occur when the stent is bent and portions of the stent project outward when the stent is in the unexpanded condition. The present invention undulating links reduce the likelihood of fishscaling.

In one embodiment, one or more sections of the stent are covered with a material such as PTFE or ePTFE. For example, the central section can be partially or completely covered with a sheath of material so that when the stent is implanted, the sheath aligns with and provides covering support for the vulnerable plaque.

The stent may be formed from a tube by laser cutting the pattern of cylindrical rings, undulating links, and central section struts in the tube. The stent also may be formed by laser cutting a flat metal sheet in the pattern of the struts, cylindrical rings, and links, and then rolling the pattern into the shape of the tubular stent and providing a longitudinal weld to form the stent.

BRIEF DESCRIPTION OF THE DRAWINGS

FIG. 1 is an elevational view, partially in section, of a stent embodying features of the invention and which is mounted on a rapid-exchange delivery catheter and positioned within an artery.

FIG. 2 is an elevational view, partially in section, similar to that shown in FIG. 1 wherein the stent is expanded within the artery, so that the stent embeds within the arterial wall.

FIG. 3 is an elevational view, partially in section, showing the expanded stent implanted within the artery after withdrawal of the rapid-exchange delivery catheter.

FIG. 4 is a plan view of a flattened stent of the invention which illustrates the pattern of the stent shown in FIGS. 1–3.

FIG. 5 is an enlarged view of a portion of the stent shown in FIG. 4 depicting an undulating link connecting portions of adjacent cylindrical rings.

FIG. 6 is an enlarged sectional view of FIG. 4 depicting several peaks of a cylindrical ring.

FIG. 7 is an enlarged sectional view of FIG. 4 depicting a Y-shaped portion of the cylindrical ring.

FIG. 8A is a side view of a stent embodying features of the invention in an unexpanded state.

FIG. 8B is a perspective view of the stent of FIG. 8A depicting the cylindrical wall defined by each cylindrical ring.

FIG. 10 is a side view of the stent depicting cylindrical rings at the end of the stent having a thicker cross-section than the rings at the center of the stent.

FIG. 11 is a plan view of a flattened stent of the invention illustrating a combination of undulating links and straight links.

FIG. 12 is a plan view of a flattened stent depicting undulating struts in the central section.

FIG. 13 is a plan view of a flattened stent depicting a covering over portions of the stent.

FIG. 14 is a plan view of a flattened stent having a drug coating on selected portions.

FIG. 15 is a cross-sectional view taken along lines 15—15 depicting the drug coating on a portion of the stent.

DETAILED DESCRIPTION OF THE PREFERRED EMBODIMENTS

Figure 9:
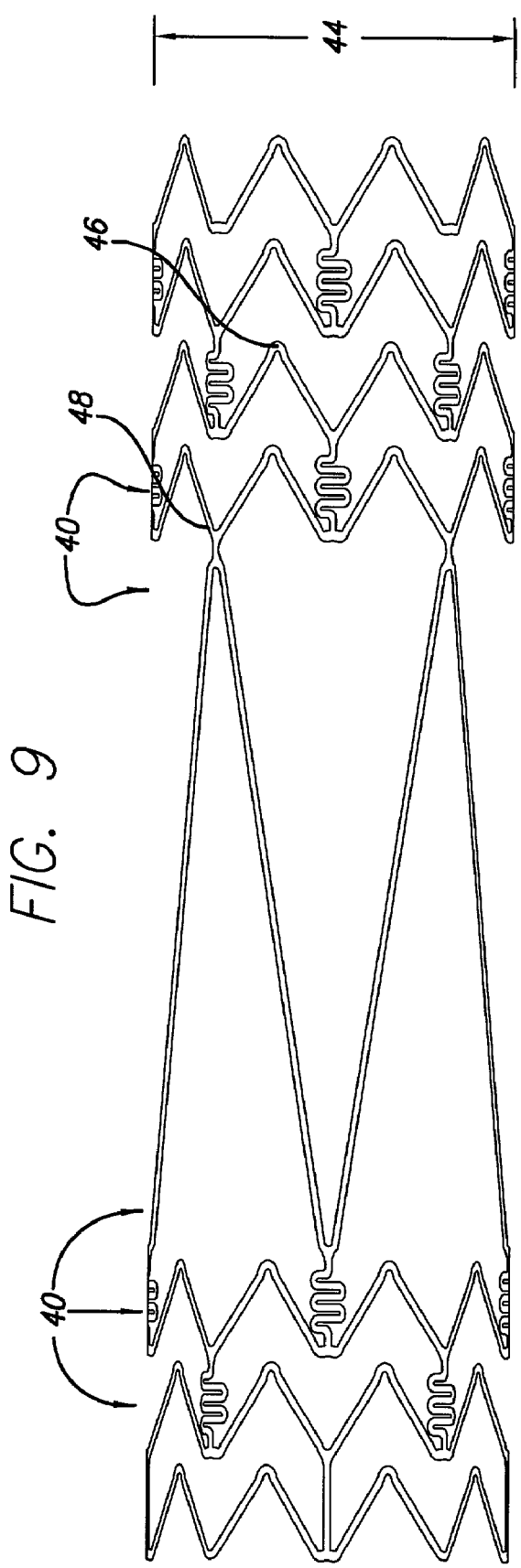
FIG. 9 is a perspective view of the stent of FIG. 8A in an expanded condition.

The present invention stent improves on existing stents by providing a longitudinally flexible stent having a uniquely designed pattern and novel interconnecting members. In addition to providing longitudinal flexibility, the stent of the present invention also provides radial rigidity and a high degree of scaffolding of a vessel wall at the stent ends and less scaffolding in the central section to intentionally promote smooth muscle cell growth. The design of the highly flexible interconnecting members and their placement nested within a W-shaped member provides for uniform scaffolding and a high degree of vessel wall coverage while the struts of the central section provide comparatively minimal vessel wall coverage.

Turning to the drawings, FIG. 1 depicts the present invention stent 10 mounted on a catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque 26 that has been previously treated by an angioplasty or other repair procedure. Stent 10 of the present invention is used to repair a diseased or damaged arterial wall which may include the plaque 26 as shown in FIG. 1, or vulnerable plaque 27 which is commonly found in the coronary arteries, peripheral arteries and other vessels. Vulnerable plaque consists of a thrombogenic lipid 28 that is covered by a thin fibrous cap 29. The stent of the invention is configured to repair the vessel having both plaque and vulnerable plaque.

In a typical procedure to implant stent 10, the guide wire 18 is advanced through the patient's vascular system by well known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 serves to hold open the artery after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with smooth muscle cell growth which further minimizes blood flow interference. The undulating portion of the stent provides good tacking characteristics to prevent stent movement within the artery.

In keeping with the present invention, FIGS. 4–11 depict stent 10 in various configurations. Turning to FIG. 4, stent 10 is shown in a flattened condition so that the pattern can be clearly viewed, even though the stent is never in this form. The stent is typically formed from a tubular member, however, it can be formed from a flat sheet such as shown in FIG. 4 and rolled into a cylindrical configuration.

The stent of the present invention is particularly useful in treating vulnerable plaque 27 which generally comprises a thrombogenic lipid 28 that has accumulated and is covered by a thin fibrous cap 29. As shown in FIGS. 4–11, the stent is designed to have three sections, a distal section 30, a proximal section 31, and a central section 32. The distal section and the proximal section typically include cylindrical rings 40 which are connected by one or more links 54, both of which will be further described herein. With respect to the central section 32, it is designed to be aligned with the vulnerable plaque in the area of the fibrous cap so that after the stent is implanted, smooth muscle cells will accumulate and readily grow over the central section thereby reinforcing the fibrous cap and preventing rupture, and thence emboli in the form of the released thrombogenic lipid. The central section 32 includes struts 33 which are depicted as straight struts 34, however, the struts can have undulating member 35 as shown in FIG. 12. The straight struts 34 or the undulating struts 35 are connected by apices 36, which are typically curved to enhance stent expansion. Together the struts and apices form the connection between the distal section 30 and the proximal section 31. It has been shown through empirical data that increasing the number of struts per cross-section provides an associated drop in neointimal thickening after a short period of time. In other words, the distal section 30 and the proximal section 32 have a higher density of struts in the form of cylindrical rings and links than does the central section 32 having struts 33. Based on the empirical data, the struts 33 will promote development of neointimal thickness along the struts which are aligned with the fibrous cap, thereby providing a thickening of cell growth over the fibrous cap and reinforcing the area in order to prevent rupture of the thrombogenic lipid into an artery or other vessel.

The stent 10 of the present invention also can be described has having a first strut pattern 37A and a second strut pattern 37B in the distal section 30 and the proximal section 31, respectively. A third strut pattern 37C is formed in the central section and includes struts 33 which can either be straight 34 or undulating struts 35. The straight struts and the undulating struts are connected by apices 36 and the struts and apices together form the connection between the first strut pattern in the distal section 30 and the second strut pattern in the proximal section 31.

With respect to the structure of the cylindrical rings and links, virtually any pattern is acceptable as long as the pattern of struts are more dense than the strut pattern in the central section 32. Typically, the rings are in the form generally of a zig-zag pattern 38 that can easily expand radially outwardly or compress radially inwardly. Thus, as described immediately below, several examples of cylindrical rings 40 and links 54 are described, however, other patterns are envisioned that would perform equally as well in inhibiting growth of smooth muscle cells at the stent proximal and distal ends and more specifically in the distal section 30 and the proximal section 31.

As shown in FIGS. 4–11, stent 10 is made up of a plurality of cylindrical rings 40 which extend circumferentially around the stent when it is in a tubular form (see FIG. 8). The stent has a delivery diameter 42 as shown in FIG. 8, and an implanted diameter 44 as shown in FIG. 9. Each cylindrical ring 40 has a cylindrical ring proximal end 46 and a cylindrical ring distal end 48. Typically, since the stent is laser cut from a solid tube there are no discreet parts such as the described cylindrical rings. However, it is beneficial for identification and reference to various parts to refer to the cylindrical rings and the following parts of the stent.

Each cylindrical ring 40 defines a cylindrical plane 50 which is a plane defined by the proximal and distal ends 46, 48 and the circumferential extent as the cylindrical ring travels around the cylinder. Each cylindrical ring includes cylindrical outer wall surface 52 which defines the outermost surface of the stent, and cylindrical inner wall surface 53 which defines the innermost surface of the stent. Cylindrical plane 50 follows the cylindrical outer wall surface.

In keeping with the invention, undulating link 54 is positioned within cylindrical plane 50. The undulating links connect one cylindrical ring to an adjacent cylindrical ring and provide overall longitudinal flexibility to the stent due to their unique construction. The flexibility of undulating links derives in part from bends 56 connected to straight portions 58 wherein the straight portions are substantially perpendicular to the longitudinal axis of the stent. Thus, as the stent is being delivered through a tortuous vessel, such as a coronary artery, the bends 56 and straight portions 58 of the undulating links will permit the stent to flex in the longitudinal direction which substantially enhances delivery of the stent to the target site. The number of bends and straight portions can be increased or decreased from that shown, to achieve differing flexibility constructions. With the straight portions being substantially perpendicular to the stent longitudinal axis, the undulating link acts like a hinge to provide flexibility. A straight link that is parallel to the stent axis typically is not flexible and does not add to the flexibility of the stent.

Cylindrical rings 40 can be nested such that adjacent rings slightly overlap in the longitudinal direction so that one ring is slightly nested within the next ring and so on. The degree of nesting is dictated primarily by the length of each cylindrical ring, the number of undulations in the rings, the thickness of the struts that make up the rings, and the radius of curvature, all in conjunction with the crimped or delivery diameter of the stent. If the rings are substantially nested one within the other, it may be difficult to crimp the stent to an appropriate delivery diameter without the various struts overlapping. It is also contemplated that the rings are slightly nested even after the stent is expanded, which enhances vessel wall coverage. In some circumstances, it may not be desirable to nest one ring within the other, which is also contemplated by the invention.

Referring to FIGS. 4–11, the stent 10 can be described more particularly as having a plurality of peaks 70 and valleys 72. Although the stent is not divided into separate elements, for ease of discussion references to peaks and valleys is appropriate. The number of peaks and valleys, sometimes referred to as crowns, can vary in number for each ring depending upon the application. Thus, for example, if the stent is to be implanted in a coronary artery, a lesser number of peaks and valleys (or crowns) are required than if the stent is implanted in a peripheral artery, which has a larger diameter than a coronary artery. As can be seen in FIG. 4, peaks 70 are in phase 74, meaning that the peaks 70 are substantially aligned along the longitudinal axis of the stent. It may be desirable under certain circumstances to position peaks 70 so that they are out of phase (not shown), that is, the peaks of one ring would be circumferentially offset from the peaks of an adjacent ring. As shown in FIG. 4, the peaks are circumferentially offset 77 from the valleys and from the undulating link 54. Positioning the peaks, valleys, and undulating links in this manner, provides a stent having uniform expansion capabilities, high radial strength, a high degree of flexibility, and sufficient wall coverage to support the vessel.

Referring to FIGS. 5–7, the stent of the invention can be described as having cylindrical rings formed of U-shaped portions 90, Y-shaped portions 92, and W-shaped portions 94. Again, while the stent is generally laser cut from a solid tube and it typically has no discreet parts, for ease of identification the stent of the invention also can be referred to as having U-, Y-, and W-shaped portions. The U-shaped portions have not supporting structure attached thereto. The Y-shaped portions, at their base, or apex, have arm 68 extending therefrom and attached to undulating link 54. The W portion has at its base or curve portion arm 69 which attaches at the other end of the undulating link. The length of the arms attaching the links to the rings can vary. Importantly, the arms should be sized in conjunction with the undulating link so that the link is properly positioned in the W-shaped portion. Preferably, undulating link 54 is contained within W-shaped portion 94, which should be wide enough to accommodate the undulating link when the stent is crimped so that no portion of the undulating link and the W-portion overlap. Preferably, the undulating link and the W-shaped portion are in the same cylindrical plane 50 as defined by the cylindrical outer wall surface 52 and the cylindrical inner wall surface 53.

In one aspect of the invention, the stent is formed so that the struts 98 (FIG. 10) have variable thickness along the stent length. As one example, it is contemplated that struts 104 at the ends of the stent may be thicker than the struts 106 in the center of the stent for purposes for radiopacity and to counter balloon expansion. When the balloon first inflates, the balloon ends have a tendency to inflate at a faster rate than the balloon center, however, with thicker struts at the stent ends the balloon, and hence the stent, will expand more uniformly.

As described above, it is also contemplated that more or fewer undulating links 54 will be positioned between adjacent cylindrical rings 40. It is also contemplated, in order to increase stent stability, that straight links 110, as shown in FIG. 11, in addition to undulating links 54, connect adjacent cylindrical rings. The straight links will provide stability and assist in preventing stent foreshortening, as do the undulating links. The straight links allow the rings to be crimped or compressed more tightly at the stent ends which aids in delivering the stent through tortuous arteries. Further, the straight links may provide more rigidity in a localized area, such as at the stent ends, such that it may be desirable to incorporate more straight links between the cylindrical rings at the stent ends, than in the center of the stent.

In one important aspect of the invention, after stent 10 is implanted in a coronary artery, or other vessel, because of its novel design, the cylindrical rings 40 have the ability to flex radially as the vessel pulsates when blood pumps through it. Likewise, because of the novel and unique design of undulating links 54, as the vessel moves and pulsates from the pumping blood, the stent can flex longitudinally. The radial and longitudinal flexing of the stent reduces the likelihood that the stent will cause injury to the intima of a coronary artery, which also may have a tendency to reduce the likelihood of restenosis.

Any portion of the disclosed stent can be made from a metal alloy or from a polymer. For example, the cylindrical rings can be made from a metal alloy while the connecting links can be made from a metal alloy or a polymer. Typically, if the links are made from a polymer, the stent will be more longitudinally flexible than if the links were made from a metal alloy. Also, the central section struts can be made from either a metal alloy or a polymer.

Exemplary of the metallic material used in forming the cylindrical rings and links of the stent is stainless steel, titanium, nickel titanium, tantalum, gold, cobalt-chromium, platinum, palladium, and iradium. Other metals, metal alloys and polymers may also be used to form the present invention stent.

Exemplary of the biocompatible polymer material used in forming the central section struts, the rings, or the links includes the group of polymers consisting of polyurethanes, polyetherurethanes, polyesterurethanes, silicone, thermoplastic elastomer (C-flex), polyether-amide thermoplastic elastomer (Pebax), fluoroelastomers, fluorosilicone elastomer, styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile rubber, a family of elastomers composed of styrene, ethylene, propylene, aliphatic polycarbonate polyurethane, polymers augmented with antioxidants, polymers augmented with image enhancing materials, polymers having a proton (H+) core, polymers augmented with protons (H+), butadiene and isoprene (Kraton) and polyester thermoplastic elastomer (Hytrel), polyethylene, PLA, PGA, and PLGA.

It may be desirable to provide a cover on one or more portions of the stent 10 of the present invention. As shown in FIG. 13, for example, stent cover 120 covers portions of the central section which will come in contact with the fibrous cap. The stent cover is used to strengthen and support the area in the fibrous cap to prevent rupture. Since only a portion of the central section is covered, the remaining open sections will develop smooth muscle cell growth over the central section struts 33 thereby further supporting the area around the vulnerable plaque 27. Portions of the distal section and proximal section 30,31 also can be covered with stent cover 120. The stent cover can include materials such as PTFE or ePTFE, or their equivalent. The stent cover can be attached to the stent by various means including adhesives or laser bonding. Further, it is desirable that the stent cover have at least some elastic properties so that as the stent expands from a delivered diameter to an implanted diameter, the stent cover does not distort or prevent stent expansion.

The stent 10 may also be used in connection with a therapeutic agent to perform a variety of functions, from preventing blood clots to promoting healing. As an example and as shown in FIGS. 14 and 15, an active agent coated 125 on struts 124 in the distal and/or proximal sections 30,31 can inhibit the activity of endothelial cells. Similarly, an active agent coated on selective cylindrical rings 12 can also inhibit the activity of smooth muscle cells. More specifically, the active agent is aimed at inhibiting abnormal or inappropriate migration and proliferation of smooth muscle cells. The active agent can also include any substance capable of exerting a therapeutic or prophylactic effect in the practice of the present invention. The agent can also be for enhancing wound healing in a vascular site or improving the structural and elastic properties of the vascular site. The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Importantly, any use of a therapeutic agent on the stent distal and proximal sections 30,31 to inhibit cell growth, must be balanced with the objective of the central section 32 to promote cell growth over the vulnerable plaque area 27.

Examples of therapeutic agents include rapamycin, actinomycin D (ActD), or derivatives and analogs thereof ActD is manufactured by Sigma-Aldrich, 1001 West Saint Paul Avenue, Milwaukee Wis. 53233, or COSMEGEN, available from Merck. Synonyms of actinopmycin D include dactinomycin, actinomycin IV, actinomycin 11, actinomycin X1, and actinomycin C1. Examples of agents include other antiproliferative substances as well as antineoplastic, antinflammatory, antiplatelet, anticoagulant, antifibrin, antithomobin, antimitotic, antibiotic, and antioxidant substances. Examples of antineoplastics include taxol (paclitaxel and docetaxel). Examples of antiplatelets,, anticoagulants, antifibrins, and antithrombins include sodium heparin, low molecular weight heparin, hirudin, argatroban, forskolin, vapiprost, prostacyclin andprostacyclin analogs, dextran, D-phe-pro-arg-chloromethylketone (synthetic antithrombin), dipyridamole, glycoprotein, llb/llla platelet membrane receptor antagonist, recombinant hirudin, thrombin inhibitor (available from Biogen), and 7E-3B® (an antiplatelet drug from Centocore). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as Captopril (available from Squibb), Cilazapril (available from Hoffman-LaRoche), or Lisinopril (available from Merck); calcium channel blockers (such as Nifedipine), colchicine fibroblast growth factor (FGF) antagonists, fish oil (omega 3-fatty acid), histamine antagonist, Lovastatin (an inhibitor of HMG-CoA reductase, a cholesterol lowering drug from Merck), monoclonal antibodies (such as PDGF receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone.

The stent 10 of the present invention can be made in many ways. One method of making the stent is to cut a thin-walled tubular member, such as stainless steel tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as is well known in the art.

After laser cutting the stent pattern the stents are preferably electrochemically polished in an acidic aqueous solution such as a solution of ELECTRO-GLO#300, sold by ELECTRO-GLO Co., Inc. in Chicago, Ill., which is a mixture of sulfuric acid, carboxylic acids, phosphates, corrosion inhibitors and a biodegradable surface active agent. Other electropolishing solutions are well known in the art. The stents may be further treated if desired, for example by applying a biocompatible coating.

Other methods of forming the stent of the present invention can be used, such as chemical etching; electric discharge machining; laser cutting a flat sheet and rolling it into a cylinder; and the like, all of which are well known in the art at this time.

The stent of the present invention also can be made from metal alloys other than stainless steel, such as shape memory alloys. Shape memory alloys are well known and include, but are not limited to, nickel titanium and nickel/titanium/vanadium. Any of the shape memory alloys can be formed into a tube and laser cut in order to form the pattern of the stent of the present invention. As is well known, the shape memory alloys of the stent of the present invention can include the type known as thermoelastic martensitic transformation, or display stress-induced martensite. These types of alloys are well known in the art and need not be further described here.

Importantly, a stent formed of shape memory alloys, whether the thermoelastic or the stress-induced martensite-type, can be delivered using a balloon catheter of the type described herein, or in the case of stress induced martensite, be delivered via a catheter without a balloon or a sheath catheter.

While the invention has been illustrated and described herein, in terms of its use as an intravascular stent, it will be apparent to those skilled in the art that the stent can be used in other body lumens. Further, particular sizes and dimensions, number of peaks per ring, materials used, and the like have been described herein and are provided as examples only. Other modifications and improvements may be made without departing from the scope of the invention.

What is claimed:

1. A method of implanting an intravascular stent for repairing a body lumen having vulnerable plaque of a predetermined length, comprising:
   providing a catheter having a proximal end and a distal end and an expandable member adjacent the distal end;
   providing an intravascular stent, mounted on the expandable member, the stent having a distal section, a proximal section, and a central section positioned between the distal section and the proximal section, the central section having a plurality of struts connected by apices to form a substantially zig zag pattern around the circumference of the stent in the central section;
   the distal section and the proximal section having cylindrical rings having a first longitudinal length, and the central section having a cylindrical ring having a second longitudinal length at least as long as the predetermined length of the vulnerable plaque, the first longitudinal length being shorter than the second longitudinal length;
   the central section struts being arranged in a substantially uniform repeating pattern forming a single ring;
   the central section struts having a substantially uniform air to metal ratio;
   inserting the catheter into the vascular system and advancing the catheter distal end so that the stent is positioned in a body lumen to be repaired;
   aligning the stent in the body lumen so that the central section substantially aligns with the area of vulnerable plaque;
   inflating the expandable member and implanting the stent in the body lumen; and
   deflating the expandable member and withdrawing the catheter from the vascular system.

2. A flexible intravascular stent for use in a body lumen, comprising:
   a distal section, a proximal section, and a central section positioned therebetween;
   the distal section and the proximal section each having a plurality of interconnected cylindrical rings, each cylindrical ring having a first delivery diameter and a second expanded diameter;
   each cylindrical ring having a proximal end and a distal end and a cylindrical wall extending circumferentially between the proximal end and the distal end of the cylindrical ring;
   the distal section and the proximal section having cylindrical rings having a first longitudinal length, and the central section having a cylindrical ring having a second longitudinal length, the first longitudinal length being shorter than the second longitudinal length;
   at least one undulating link attaching each cylindrical ring to an adjacent cylindrical ring, the undulating links being positioned substantially within the cylindrical wall of the cylindrical ring;
   the central section having a plurality of struts connected by apices and extending around the circumference of the central section, the struts and apices connecting the distal section to the proximal section, the central section struts being arranged in a substantially uniform repeating zig zag pattern forming a single central ring; and
   the central section having a substantially uniform air to metal ratio.

3. The stent of claim 2, wherein the central section struts have a straight configuration.

4. The stent of claim 2, wherein the central section struts have a substantially curved configuration.

5. The stent of claim 2, wherein the central section struts have a substantially straight section and a substantially curved section.

6. The stent of claim 2, wherein at least one undulating link comprises at least one bend connected to a substantially straight portion, the substantially straight portion being substantially perpendicular to the stent longitudinal axis.

7. The stent of claim 6, wherein the substantially straight portion of the at least one undulating link is perpendicular to the stent longitudinal axis when the stent is in the first delivery diameter configuration.

8. The stent of claim 6, wherein the substantially straight portion of the at least one undulating link is perpendicular to the stent longitudinal axis when the stent is in the second expanded diameter configuration.

9. The stent of claim 2, wherein at least one of the undulating links comprise a plurality of bends.

10. The stent of claim 2, wherein each cylindrical ring comprises a plurality of peaks and valleys.

11. The stent of claim 10, wherein two peaks are positioned between each valley.

12. The stent of claim 10, wherein the peaks of each cylindrical ring are in phase with the peaks of an adjacent cylindrical ring.

13. The stent of claim 2, wherein the undulating links are configured to provide flexibility to the stent.

14. The stent of claim 2, wherein the cylindrical rings are configured to provide flexibility to the stent.

15. The stent of claim 2, wherein the stent is formed from a tube.

16. The stent of claim 2, wherein the stent is formed from a metal alloy.

17. The stent of claim 2, wherein the stent is formed from stainless steel.

18. The stent of claim 2, wherein the stent is formed from a shape memory alloy.

19. The stent of claim 18, wherein the stent is formed from the group of shape memory alloys consisting of nickel titanium and nickel/titanium/vanadium.

20. The stent of claim 2, wherein the stent is formed from a pseudoelastic metal alloy.

21. The stent of claim 20, wherein the stent is formed from the group of pseudoelastic metal alloys consisting of nickel titanium and nickel/titanium/vanadium.

22. The stent of claim 2, wherein at least a portion of the central section is provided with a cover.

23. The stent of claim 22, wherein the stent cover is formed of a polymer.

24. The stent of claim 23, wherein the polymer cover is taken from the group of polymers including PTFE and ePTFE.

25. The stent of claim 24, wherein the stent cover is attached to the struts of the central section by an adhesive.

26. The stent of claim 25, wherein the stent cover is attached to the struts of the central section by laser bonding.

27. The stent of claim 2, wherein at least a portion of the distal section rings are coated with a therapeutic drug to reduce cell growth distal to the vulnerable plaque.

28. The stent of claim 2, wherein at least a portion of the proximal section rings are coated with a therapeutic drug to reduce cell growth proximal to the vulnerable plaque.

29. The stent of claim 2, wherein at least a portion of the distal section rings and the proximal section rings are coated with a therapeutic drug to reduce cell growth on either side of the vulnerable plaque.

30. A stent for implanting in a body lumen, comprising:
a distal section, a proximal section, and a central section positioned between the distal section and the proximal section, each section being aligned along a common longitudinal axis forming the stent;
the distal section having a first strut pattern, the proximal section having a second strut pattern, and the central section having a third strut pattern;
wherein the third strut pattern has a substantially uniform repeating series of zig-zagging struts that form a single ring;
the distal section and the proximal section having cylindrical rings having a first longitudinal length, and the central section having a cylindrical ring having a second longitudinal length, the first longitudinal length being shorter than the second longitudinal length;
the first strut pattern having a first metallic surface area;
the second strut pattern having a second metallic surface area;
the third strut pattern having a third metallic surface area;
the third strut pattern having a substantially uniform air to metal ratio; and
at least one of the first and second metallic surface areas being greater that the metallic surface area of the third strut pattern.

31. The stent of claim 30, wherein the metallic surface areas of at least one of the first and second strut pattern being less than about 20%.

32. The stent of claim 30, wherein the first, second and third strut patterns are in an expanded configuration.

33. A stent for treating vulnerable plaque, comprising:
a distal section, a proximal section, and a central section positioned between the distal section and the proximal section, each section being aligned along a common longitudinal axis forming the stent;
the distal section and the proximal section having a first strut pattern and a second strut pattern respectively, and the central section having a third strut pattern;
wherein the central section has a uniform repeating series of zig-zagging struts that form a single ring;
the distal section and the proximal section having cylindrical rings having a first longitudinal length, and the central section having a cylindrical ring having a second longitudinal length, the first longitudinal length being shorter than the second longitudinal length;
the central section having a substantially uniform air to metal ratio;
each strut pattern having curved portions and straight portions configured to allow the patterns to compress and expand; and
the third strut pattern having fewer curved portions and straight portions that the first and second strut patterns.

34. The stent of claim 33, wherein the third strut pattern is disposed between the first and the second strut patterns.

35. The stent of claim 33, wherein the first strut pattern is different than the second strut pattern.

36. The stent of claim 33, wherein the first strut pattern and the second strut pattern are substantially the same.

37. The stent of claim 33, wherein the third strut pattern is different than the first and second strut patterns.

38. The stent of claim 33, wherein the third strut pattern has an air to metal ratio that is higher than an air to metal ratio of the first or second strut pattern.

39. An intravascular stent for use in a body lumen, comprising:
a distal section, a proximal section, and a central section positioned between the distal section and the proximal section, each section being aligned along a common longitudinal axis forming the stent;
the distal section and the proximal section having cylindrical rings having a first longitudinal length, and the central section having a cylindrical ring having a second longitudinal length, the first longitudinal length being shorter than the second longitudinal length;
the distal section and the proximal section having a first strut pattern and a second strut pattern respectively, and the central section having a third strut pattern;
the third strut pattern having a substantially uniform repeating series of struts that form a single central ring wherein each strut is directly attached to an adjacent strut to define a zig-zag pattern;
the first strut pattern and the second strut pattern being more dense than the third strut pattern;
the third strut pattern having a substantially uniform air to metal ratio; and
wherein the third strut pattern includes straight struts, at least some of the straight struts having undulating members.

40. The stent of claim 39, wherein the stent is formed from a metal alloy.

41. The stent of claim 39, wherein the stent is formed from stainless steel.

42. The stent of claim 39, wherein at least a portion of the central section is provided with a polymer cover.

43. The stent of claim 39, wherein at least a portion of the distal section rings are coated with a therapeutic drug.

44. The stent of claim 39, wherein at least a portion of the proximal section rings are coated with a therapeutic drug.

45. The stent of claim 39, wherein at least a portion of the distal section rings and the proximal section rings are coated with a therapeutic drug.

46. An intravascular stent for use in a body lumen, comprising:
- a distal section, a proximal section, and a central section positioned between the distal section and the proximal section, each section being aligned along a common longitudinal axis forming the stent;
- the distal section and the proximal section having cylindrical rings having a first longitudinal length, and the central section having a cylindrical ring having a second longitudinal length, the first longitudinal length being shorter than the second longitudinal length;
- the distal section and the proximal section having a first strut pattern and a second strut pattern respectively, and the central section having a third strut pattern;
- the third strut pattern having a substantially uniform repeating series of struts that form a single central ring wherein each strut is directly attached to an adjacent strut to define a zig-zag pattern;
- the first strut pattern and the second strut pattern being more dense than the third strut pattern;
- the third strut pattern having a substantially uniform air to metal ratio; and
- wherein the third strut pattern includes undulating struts.

47. The stent of claim 46, wherein the stent is formed from a metal alloy.

48. The stent of claim 46, wherein the stent is formed from stainless steel.

49. The stent of claim 46, wherein at least a portion of the central section is provided with a polymer cover.

50. The stent of claim 46, wherein at least a portion of the distal section rings are coated with a therapeutic drug.

51. The stent of claim 46, wherein at least a portion of the proximal section rings are coated with a therapeutic drug.

52. The stent of claim 46, wherein at least a portion of the distal section rings and the proximal section rings are coated with a therapeutic drug.

53. An intravascular stent for use in a body lumen, comprising:
- a distal section, a proximal section, and a central section positioned between the distal section and the proximal section, each section being aligned along a common longitudinal axis forming the stent;
- the distal section and the proximal section having cylindrical rings having a first longitudinal length, and the central section having a cylindrical ring having a second longitudinal length, the first longitudinal length being shorter than the second longitudinal length;
- the distal section and the proximal section having a first strut pattern and a second strut pattern respectively, and the central section having a third strut pattern;
- the third strut pattern having a substantially uniform repeating series of struts that form a single central ring wherein each strut is directly attached to an adjacent strut to define a zig-zag pattern;
- the first strut pattern and the second strut pattern being more dense than the third strut pattern; and
- the third strut pattern having a substantially uniform air to metal ratio; and
- wherein the distal section and the proximal section each have a plurality of cylindrical rings interconnected along the longitudinal axis by links.

54. The stent of claim 53, wherein the stent is formed from a metal alloy.

55. The stent of claim 53, wherein the stent is formed from stainless steel.

56. The stent of claim 53, wherein at least a portion of the central section is provided with a polymer cover.

57. The stent of claim 53, wherein at least a portion of the distal section rings are coated with a therapeutic drug.

58. The stent of claim 53, wherein at least a portion of the proximal section rings are coated with a therapeutic drug.

59. The stent of claim 53, wherein at least a portion of the distal section rings and the proximal section rings are coated with a therapeutic drug.

60. The stent of claim 53, wherein the links have a substantially straight configuration.

61. The stent of claim 53, wherein the links have an undulating configuration.

62. The stent of claim 53, wherein the links have a straight section and an undulating section.

63. The stent of claim 53, wherein the links have a straight section and a curved section.

* * * * *

UNITED STATES PATENT AND TRADEMARK OFFICE
CERTIFICATE OF CORRECTION

PATENT NO. : 7,163,553 B2 Page 1 of 1
APPLICATION NO. : 10/034208
DATED : January 16, 2007
INVENTOR(S) : Timothy A. Limon It is certified that error appears in the above-identified patent and that said Letters Patent is hereby corrected as shown below:

<u>Title page</u>, Item 57, ABSTRACT, delete "for a an intravascular stent" and insert --for an intravascular stent--.

<u>Column 2</u>,
Line 51, delete "a undulating or serpentine" and insert --an undulating or a serpentine--.

<u>Column 9</u>,
Line 9, delete "iradium" and insert --iridium--.

<u>Column 13</u>,
Line 61, delete "that" and insert --than--.

<u>Column 14</u>,
Line 22, delete "that" and insert --than--.

Signed and Sealed this

Seventeenth Day of April, 2007

JON W. DUDAS
*Director of the United States Patent and Trademark Office*